(12) United States Patent (10) Patent No.: US 7,338,431 B2
Baugh (45) Date of Patent: Mar. 4, 2008

(54) METHOD AND APPARATUS TO STIMULATE THE IMMUNE SYSTEM OF A BIOLOGICAL ENTITY

(76) Inventor: Carl E. Baugh, 3102 FM 205, P.O. Box 209, Glen Rose, TX (US) 76043

( * ) Notice: Subject to any disclaimer, the term of this patent is extended or adjusted under 35 U.S.C. 154(b) by 298 days.

(21) Appl. No.: 11/038,781

(22) Filed: Jan. 19, 2005

(65) Prior Publication Data
US 2005/0171397 A1 Aug. 4, 2005

Related U.S. Application Data

(63) Continuation-in-part of application No. 10/114,656, filed on Apr. 2, 2002, now Pat. No. 6,902,521.

(60) Provisional application No. 60/281,203, filed on Apr. 3, 2001.

(51) Int. Cl.
*A61N 2/02* (2006.01)

(52) U.S. Cl. .......................... 600/13
(58) Field of Classification Search .......... 600/9–15
See application file for complete search history.

(56) References Cited

U.S. PATENT DOCUMENTS

| | | | |
|---|---|---|---|
| 1,391,762 A | 9/1921 | Dequer | |
| 1,841,509 A | 1/1932 | Van Damme et al. | |
| 3,557,753 A | 1/1971 | Dantoni | |
| 3,658,051 A | 4/1972 | MacLean | |
| 3,678,337 A | 7/1972 | Grauvogel | |
| 3,890,486 A * | 6/1975 | Fitzgerald | 219/523 |
| 4,315,503 A * | 2/1982 | Ryaby et al. | 600/14 |
| 4,428,366 A * | 1/1984 | Findl et al. | 600/14 |
| 4,493,480 A | 1/1985 | Nichol | |
| 4,825,588 A | 5/1989 | Norman | |
| 5,014,699 A | 5/1991 | Pollack et al. | |
| 5,087,353 A | 2/1992 | Todd et al. | |
| 5,192,874 A | 3/1993 | Adams | |
| 5,195,940 A | 3/1993 | Baylink | |
| 5,224,922 A | 7/1993 | Kurtz | |
| 5,277,692 A | 1/1994 | Ardizzone | |
| 5,304,111 A | 4/1994 | Mitsuno et al. | |
| 5,338,286 A | 8/1994 | Abbott et al. | |
| 5,480,373 A | 1/1996 | Fischer et al. | |
| 5,576,694 A | 11/1996 | Touchton et al. | |

(Continued)

OTHER PUBLICATIONS

International Search Report, PCT/US06/01735, Feb. 26, 2007.

(Continued)

*Primary Examiner*—Samuel G Gilbert
(74) *Attorney, Agent, or Firm*—Hahn Loeser & Parks, LLP; David J. Muzilla

(57) ABSTRACT

A system and method for stimulating the immune systems of biological entities in an environment are disclosed. Pulsed electrical currents are generated using an electric current generator. The pulsed electrical currents are fed through an arrangement of electrically conductive material such that magnetic energy is emitted from the arrangement into the environment. The arrangement of electrically conductive material is designed such that an intensity of the emitted magnetic energy varies across at least one spatial dimension of the environment. Certain embodiments of the arrangement, which have width-to-length ratios of approximately 0.6, tend to provide variations in the intensity of the magnetic energy field which are very good for stimulating the immune systems of the biological entities.

12 Claims, 15 Drawing Sheets

U.S. PATENT DOCUMENTS

| | | | |
|---|---|---|---|
| 5,595,564 | A | 1/1997 | Pinna |
| 5,741,317 | A | 4/1998 | Ostrow |
| 5,935,516 | A | 8/1999 | Baugh |
| 6,004,257 | A | 12/1999 | Jacobson |
| 6,119,631 | A * | 9/2000 | Markoll ............ 119/417 |
| 6,203,486 | B1 | 3/2001 | Miller et al. |
| 6,398,455 | B1 | 6/2002 | Volstad |
| 6,497,648 | B1 * | 12/2002 | Rey ............ 600/14 |
| 6,519,131 | B1 | 2/2003 | Beck |
| 6,558,311 | B1 | 5/2003 | Muntermann |
| 6,663,556 | B2 * | 12/2003 | Barker ............ 600/14 |
| 2003/0056432 | A1 | 3/2003 | Prevost |
| 2004/0133060 | A1 | 7/2004 | Wilhelm et al. |

OTHER PUBLICATIONS

Namba, K. et al., (1995) "Effect of Magnetic Field On Germination and Plant Growth." Acta Horticulturae, 399, 143-147.

Matsuda, T. et al., (1993) "Influences of Magnetic Fields on Growth and Fruit Production of Strawberry," Acta Horticulurae, 348, p. 378-380.

Ginzo, H.D. and Decima, E.E. (1995) "Weak Static Magnetic Fields Increase the Speed of Circumnutation in Cucumber Tendris," Experientia, 51, p. 1090-1094.

Baker, R.R. (1980) "Goal Orientation by Blindfolded Humans After Long-Distance Displacement: Possible Involvement of a Magnetic Sense," Science, 210, p. 555-557.

Richter, K., Bohm, G.A. & Rembold, H. (1995) "Head Critical Period and Juvenile Hormone Titre During The Last Larval Instar of the Cockroach, *Periplaneta americana*", Experientia 51, p. 1094-1096.

* cited by examiner

METHOD AND APPARATUS TO STIMULATE THE IMMUNE SYSTEM OF A BIOLOGICAL ENTITY

CROSS-REFERENCE TO RELATED APPLICATIONS/INCORPORATION BY REFERENCE

This U.S. patent application is a continuation-in-part (CIP) of U.S. patent application Ser. No. 10/114,656, filed on Apr. 2, 2002, now U.S. Pat. No. 6,902,521, which claims the benefit of U.S. Provisional Patent Application Ser. No. 60/281,203 filed Apr. 3, 2001, both applications hereby incorporated by reference.

TECHNICAL FIELD

Certain embodiments of the present invention relate to stimulating the immune system of biological entities. More particularly, certain embodiments of the present invention relate to a system and method to stimulate the immune system of biological entities moving in an environment through application of pulsed magnetic energy.

BACKGROUND OF THE INVENTION

Use of magnetic energy to increase physiological performance of organisms has long been attempted. However, many of these techniques have been limited to belts, pads or mats which apply magnetic or electromagnetic energy to the person or other organism. Problems inherent in these techniques include the necessity for the organism to wear the belt or pad, and the necessity for a portable power source in order to generate magnetic energy. Furthermore, these techniques do not effect the environment surrounding the organism. Accordingly, there is a demand for an apparatus and method of applying pulsed magnetic energy to an organism (i.e., a biological entity) and its surrounding environment that is without the aforementioned disadvantages.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

An embodiment of the present invention comprises a system for stimulating immune systems of living biological entities in an environment. The system comprises at least one electric current generator providing a source of pulsed electrical current. The system further comprises at least one continuous coil of electrically conductive material having a first end and a second end, both of the ends being connected to the at least one generator to form a closed circuit such that the at least one coil emits a spatially non-uniform pulsed magnetic field into the environment in response to the pulsed electrical current to stimulate the immune systems as the biological entities move within the environment. Also, a configuration of the at least one coil comprises a plurality of turns of the conductive material in substantially a single spatial plane, and wherein the coil has an overall width-to-length ratio of between 0.4 and 0.8.

Another embodiment of the present invention comprises a system for stimulating immune systems of biological entities in an environment. The system comprises at least one electric current generator providing a source of pulsed electrical current. The system further comprises at least one arrangement of electrically conductive material having a first end and a second end, both of the ends being connected to the at least one generator to form a closed circuit such that the at least one arrangement emits a spatially non-uniform pulsed magnetic field into the environment in response to the pulsed electrical current to stimulate the immune systems as the biological entities move within the environment. Also, a configuration of the at least one arrangement comprises a plurality of substantially parallel segments of the conductive material forming a flat, substantially rectangular grid having an overall width-to-length ratio of between 0.4 and 0.8.

A further embodiment of the present invention comprises a method for stimulating immune systems of living biological entities in an environment. The method comprises positioning at least one arrangement of electrically conductive material below a surface of the environment and connecting the at least one arrangement of electrically conductive material to at least one electric current generator to form a closed circuit through the arrangement. The method further comprises generating a pulsed electrical current with the generator such that the pulsed electrical current propagates through the arrangement from a first end of the arrangement to a second end of the arrangement. The arrangement emits pulsed magnetic energy into the environment in response to the pulsed electrical current such that an intensity of the pulsed magnetic energy is non-uniform across at least one spatial dimension of the arrangement to stimulate the immune systems as the biological entities move within the environment.

Another embodiment of the present invention includes a system for stimulating the immune systems of biological entities in an environment. The system comprises at least one electric current generator providing a source of pulsed electrical current. The system further comprises at least one continuous coil of electrically conductive material having a first end and a second end where both ends are connected to the generator to form a closed circuit such that the coil emits a spatially non-uniform pulsed magnetic field into the environment in response to the pulsed electrical current to stimulate the immune systems as the biological entities move within the environment. A configuration of the coil includes a plurality of parallel straight segments of the conductive material, being substantially of the same length, and a plurality of curved segments of the conductive material. The continuous coil spirals outward from a central position of the coil in substantially a single spatial plane.

A further embodiment of the present invention includes a system for stimulating the immune systems of biological entities in an environment. The system comprises at least one electric current generator providing a source of pulsed electrical current. The system further comprises at least one continuous coil of electrically conductive material having a first end and a second end where both ends are connected to the generator to form a closed circuit such that the coil emits a spatially non-uniform pulsed magnetic field into the environment in response to the pulsed electrical current to stimulate the immune systems as the biological entities move within the environment. A configuration of the coil comprises a first plurality of parallel straight segments of the conductive material and a second plurality of parallel straight segments of the conductive material being substantially perpendicular to the first plurality of segments. The continuous coil winds outward from a central position of the coil in substantially a single spatial plane.

These and other advantages and novel features of the present invention, as well as details of illustrated embodiments thereof, will be more fully understood from the following description and drawings.

DETAILED DESCRIPTION OF THE INVENTION

Reference will now be made in detail to the various embodiments of the present invention, examples of which are illustrated in the accompanying drawings. Whenever possible, the same reference numbers will be used throughout the drawings to refer to the same or like parts.

Figure 1:
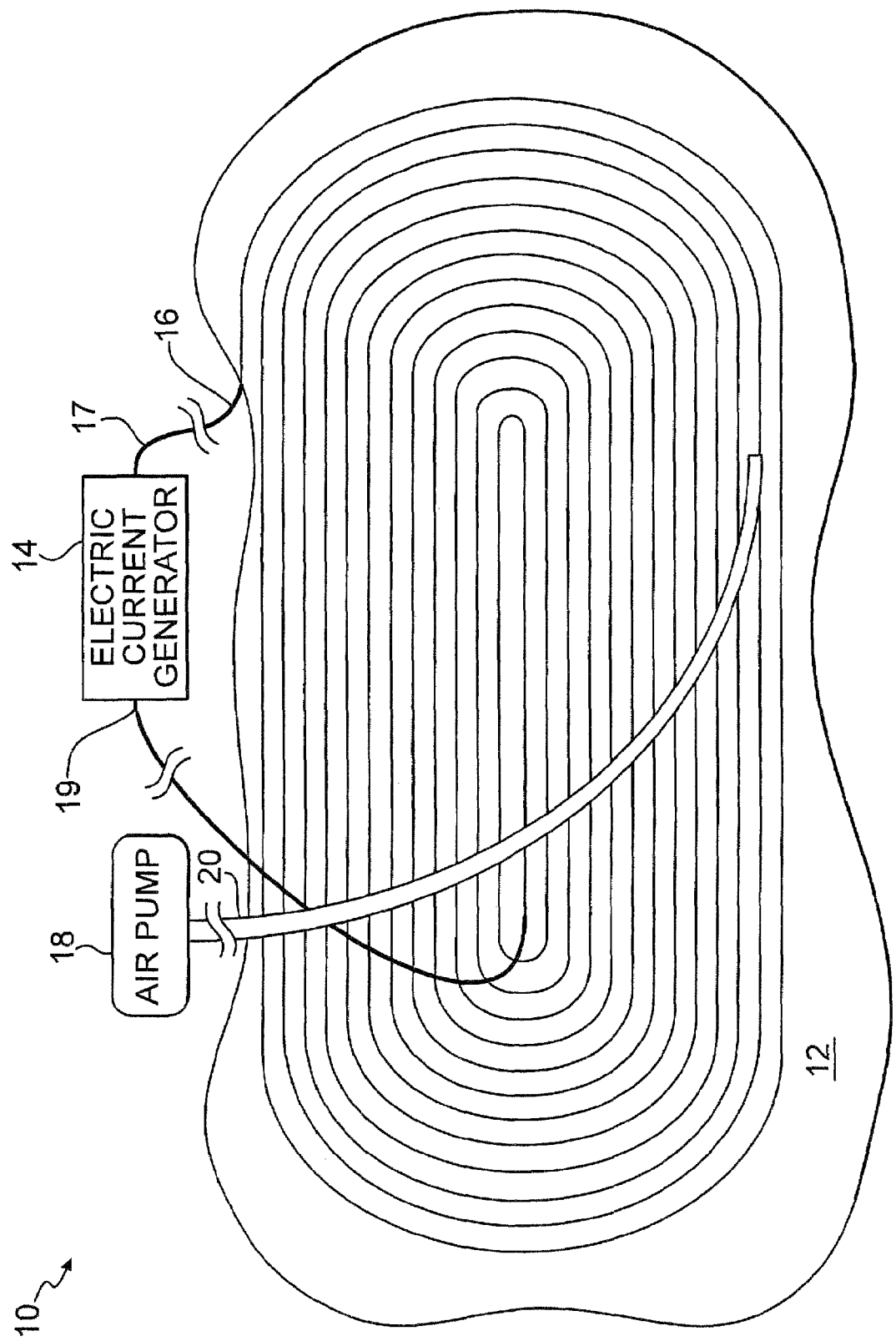
FIG. 1 illustrates a first exemplary embodiment of a system for applying pulsed magnetic energy to an aquatic environment, in accordance with various aspects of the present invention.

FIG. 1 illustrates a first exemplary embodiment of a system for applying pulsed magnetic energy to an aquatic environment, in accordance with various aspects of the present invention. Shown generally at 10, the embodiment of FIG. 1 includes a water reservoir 12, such as an aquarium, a pool, a pond or some other body of water. Below water reservoir 12 is placed electric wiring 16. In FIG. 1 electric wiring 16 is shown as a continuous coil of wiring, originating from the electric current generator 14 at a first end 17 and connecting back to the electric current generator 14 at a second end 19 to form a closed circuit. The electrical wiring 16 is placed over a substantial area of the water reservoir 12, at 1 to 30 inches below the bottom surface of the water reservoir 12, and is insulated from the surrounding elements and cross currents from other cables that may be present. If the water reservoir 12 has sides, such as in a pool, electric wiring 16 can also be placed behind the surface of the sides of reservoir 12. Electric wiring 16 is insulated by neutral materials, such as plastics, that will insulate the electric wiring 16, yet not produce a significant charge in the surrounding soil or substance. The electric wiring may be coated with an insulating material or may be placed in a non-conductive conduit, for example. Further, highly shielded electrical wire (e.g., using a conductive shield) is not desired as it decreases the capacity of diffusion of the pulsed magnetic energy into the aquatic environment. A pulsed DC voltage waveform is supplied to the electric wiring 16, and is controlled by the electric current generator 14. Pulsed current supplied by the generator 14 propagates from a first end 17 of the coil 16 to a second end 19 of the coil 16 in a closed loop in response to the pulsed DC voltage waveform. That is, both ends 17 and 19 of the coil 16 are connected to output terminals of the generator 14. Alternatively, pulsed current supplied by the generator 14 may propagate from the second end 19 to the first end 17.

Optionally, an air pump 18 and perforated air hose 20 may be included in the system embodied in FIG. 1. Air pump 18 and air hose 20 provide an oxygen source to the water within reservoir 12, thus, aerating the water and increasing the oxygen concentration of the water.

In use, pulsed electrical current is applied to the electric wiring 16 by an electric current generator 14. Various electronic components may be utilized to generate electric current for use in this system and may include a computer controlled subsystem, for example, to control the intensity and pulsed frequency of the emitted magnetic energy. An electric current generator typically includes a power transformer, a rectifier and filter circuit, and an electronic switching circuit. For example, an electric current generator may be plugged into a 240 VAC single phase power source and output a pulsed DC voltage waveform having a maximum peak amplitude of, for example, 80 VDC.

In accordance with an embodiment of the present invention, the magnetic energy emitted from the wiring 16 has magnetic field components in the range of about 0.5 to 30 Gauss, and the frequency range of the pulses is between 0.5 and 30 Hertz. Concurrently, air pump 18 pumps air through hose 20 to increase the oxygen concentration of the water. The water in free motion around the air bubbles is energized to a higher state because of the application of the pulsed magnetic energy, and thus may become even more saturated with oxygen.

Application of the magnetic energy to the reservoir 12 provides for application of magnetic energy to both plants and animals (i.e., biological entities) situated within the aquatic system. The affected plants and animals exhibit enhanced physiologic effects such as increased growth and overall health, for example, due to stimulation of the immune systems of the plants and animals. Furthermore, the highly oxygenated and energized water can then be utilized for watering plants which may not be directly exposed to the magnetic energy.

Electric current flows in a wire when a potential difference (i.e., a voltage) is applied across both ends of the wire. When electric current flows through a wire, a magnetic field is set up or emanates from the wire. If the wire is arranged in a coiled or grid-like configuration, for example, the magnetic fields from the various turns of the coil may combine constructively and destructively to form a spatially non-uniform magnetic field profile.

Figure 2:
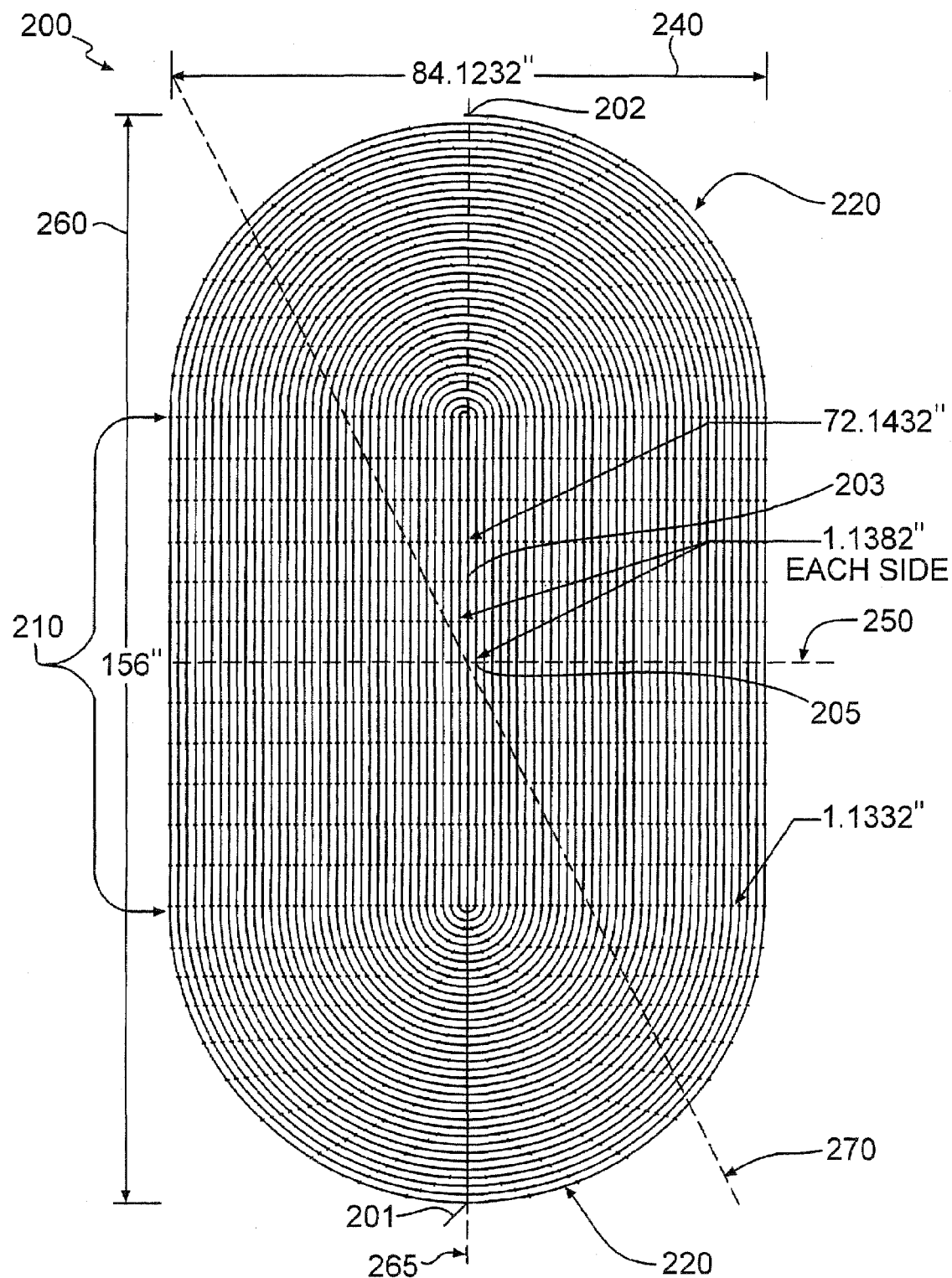
FIG. 2 illustrates a first exemplary embodiment of a flat coil used to generate magnetic energy, in accordance with various aspects of the present invention.

FIG. 2 illustrates an exemplary embodiment of a flat coil 200 used to generate magnetic energy, in accordance with various aspects of the present invention. The coil is a continuous coil of electrically conductive material (e.g., copper wire) having a first end 201 and a second end 202. Both ends 201 and 202 are connected to at least one generator (e.g. generator 14 in FIG. 1) to form a closed circuit. The generator creates a pulsed voltage waveform (e.g., a DC pulsed waveform) that results in pulsed electrical currents that propagate through the coil 200 from the first end 201 to the second end 202 (or vice versa).

When the current pulses propagate through the coil 200, magnetic energy is emitted from the coil in the form of a pulsed magnetic field. When the coil is placed in an environment such as, for example, a swimming pool, a livestock yard, a garden, orchards, an athletic ground, a play ground, a pond, a lake, a whirl pool, a hot tub, or an aquarium, the magnetic energy is dispersed into the environment. The magnetic energy tends to stimulate the immune systems of biological entities (e.g., plants, animals, and humans) that are moving within the environment.

In accordance with an embodiment of the present invention, a configuration of the coil 200 comprises a plurality of spiraling turns of a conductive material such as, for example, copper wire. The spiraling turns do not necessarily follow a strictly mathematical spiral, but rather, the turns spiral at least in the sense that the turns wrap around on each other from the inside (i.e., from a central position 203 of the coil 200) to the outside of the coil 200. The configuration forms a flat, substantially oval surface having a width-to-length ratio of between 0.4 and 0.8. Ideally, the width-to-length ratio is 0.618 which is the "golden mean" ratio found in many instances of nature. For example, the width-to-length ratio of the coil 200 shown in FIG. 2 is 84.1232 inches divided by 156 inches which is a ratio of 0.539. The coil 200 of FIG. 2 has approximately 37 turns spaced at approximately 1 inch separation. In accordance with an embodiment of the present invention, the coil 200 comprises 8 Gage solid copper wire having a resistance of about 0.6 ohms per 1000 feet.

The configuration of the coil 200 includes a plurality of parallel straight segments 210 of insulated copper wire being of substantially the same length, and a plurality of curved segment of insulated copper wire 220. The segments 210 and 220 are not discrete in the sense that they must be connected to form the coil 200. Instead, the coil 200 is a continuous piece of copper wire. However, in an alternative embodiment the coil 200 could be made from discrete segments that are connected together by, for example, welding or soldering. The configuration of the coil 200 is such that the plurality of turns of the coil are substantially in a single spatial plane, which gives the coil 200 its flat shape.

In accordance with the embodiment of FIG. 2, the coil emits a magnetic field at least perpendicular to the surface of the coil (i.e., out of the page of FIG. 2). The intensity of the magnetic field varies (i.e., is non-uniform) across the coil 200, in a spatial dimension which is parallel to the surface of the coil 200. The variation may be non-linear, in accordance with certain embodiments of the present invention. Therefore, as a biological entity moves within the environment in which the coil 200 is placed, the biological entity experiences the variations of the magnetic field. The variations stimulate the immune system of the biological entity. Typically, the coil 200 is insulated using a non-conducting material such as a plastic, to prevent direct conduction of the electrical currents into the surrounding environment.

Figure 3A:
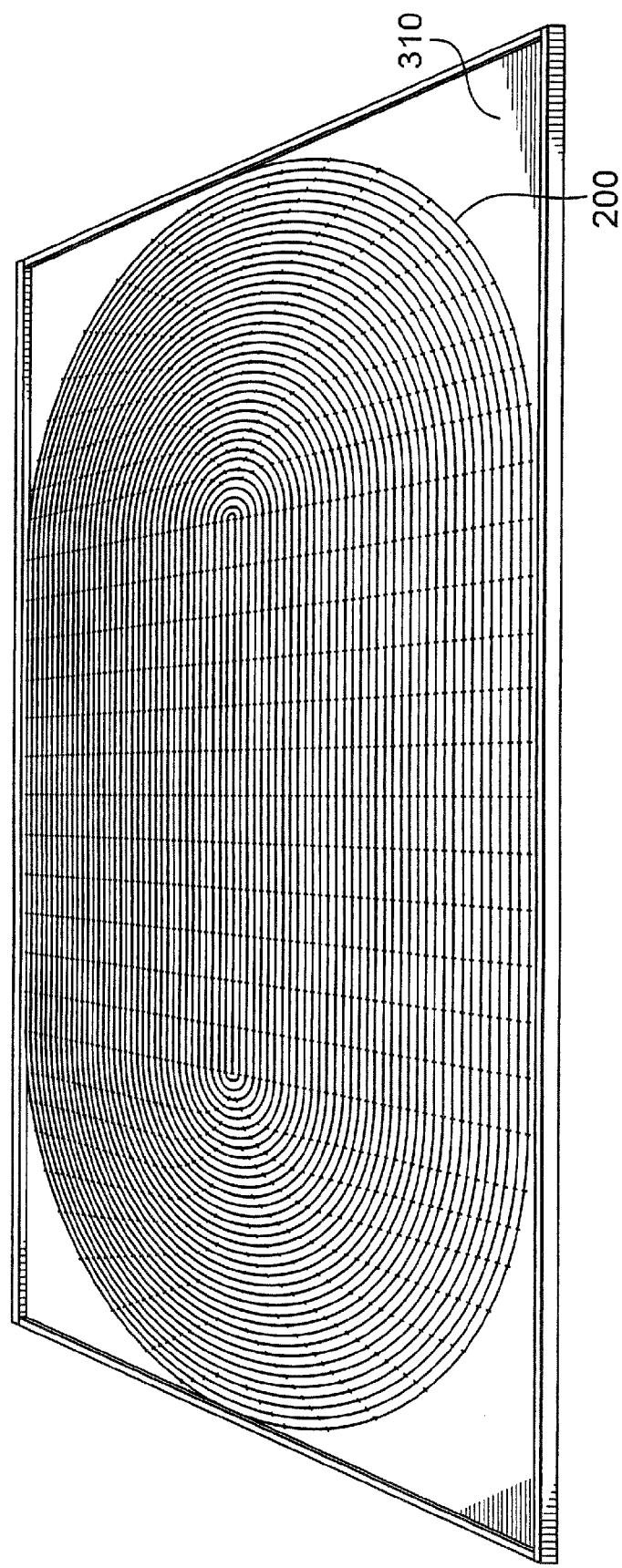
FIGS. 3A-3C illustrate various views of an embodiment of the flat coil of FIG. 2, clearly showing the spacing between the coil turns, in accordance with various aspects of the present invention.
Figure 3B:
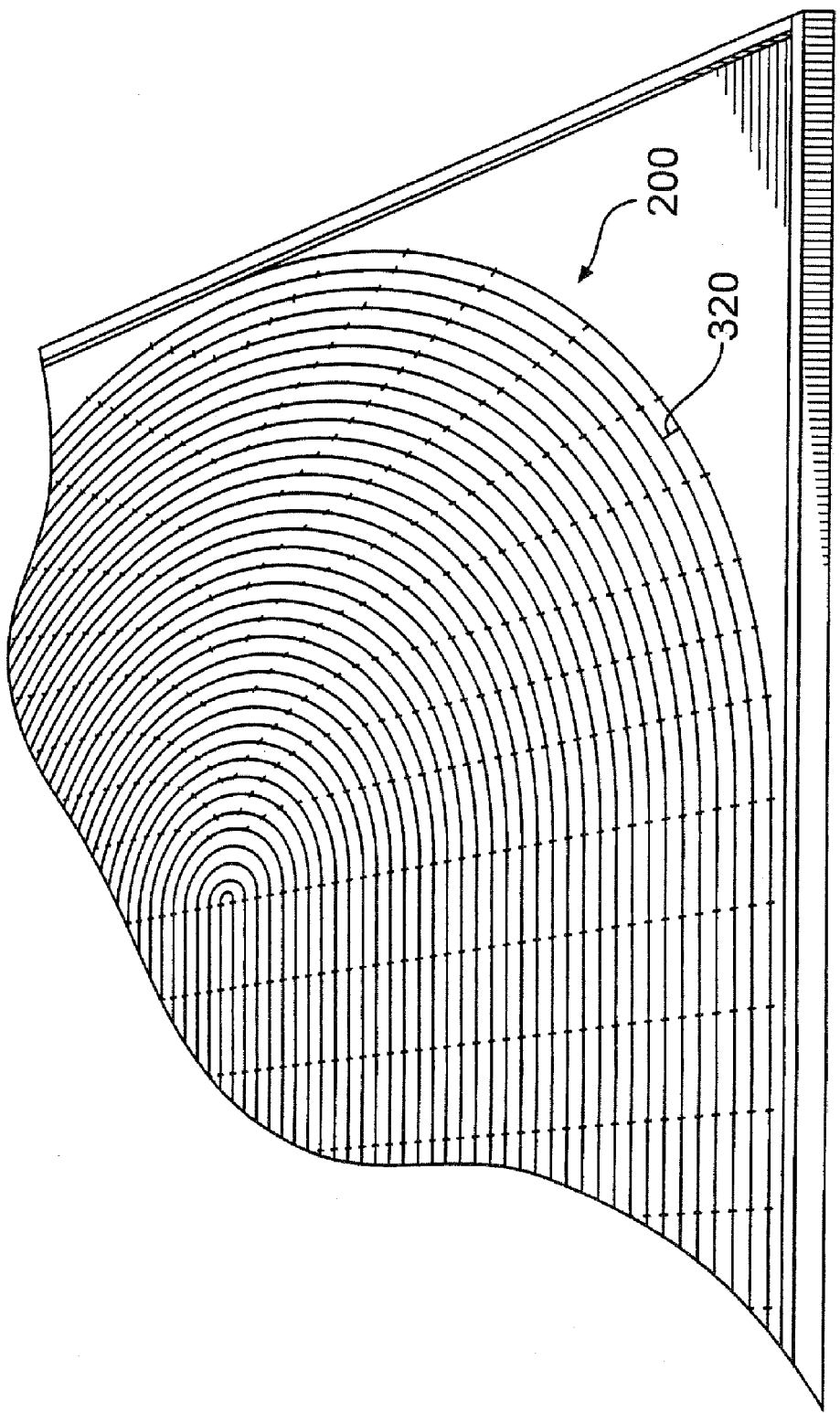
Figure 3C:
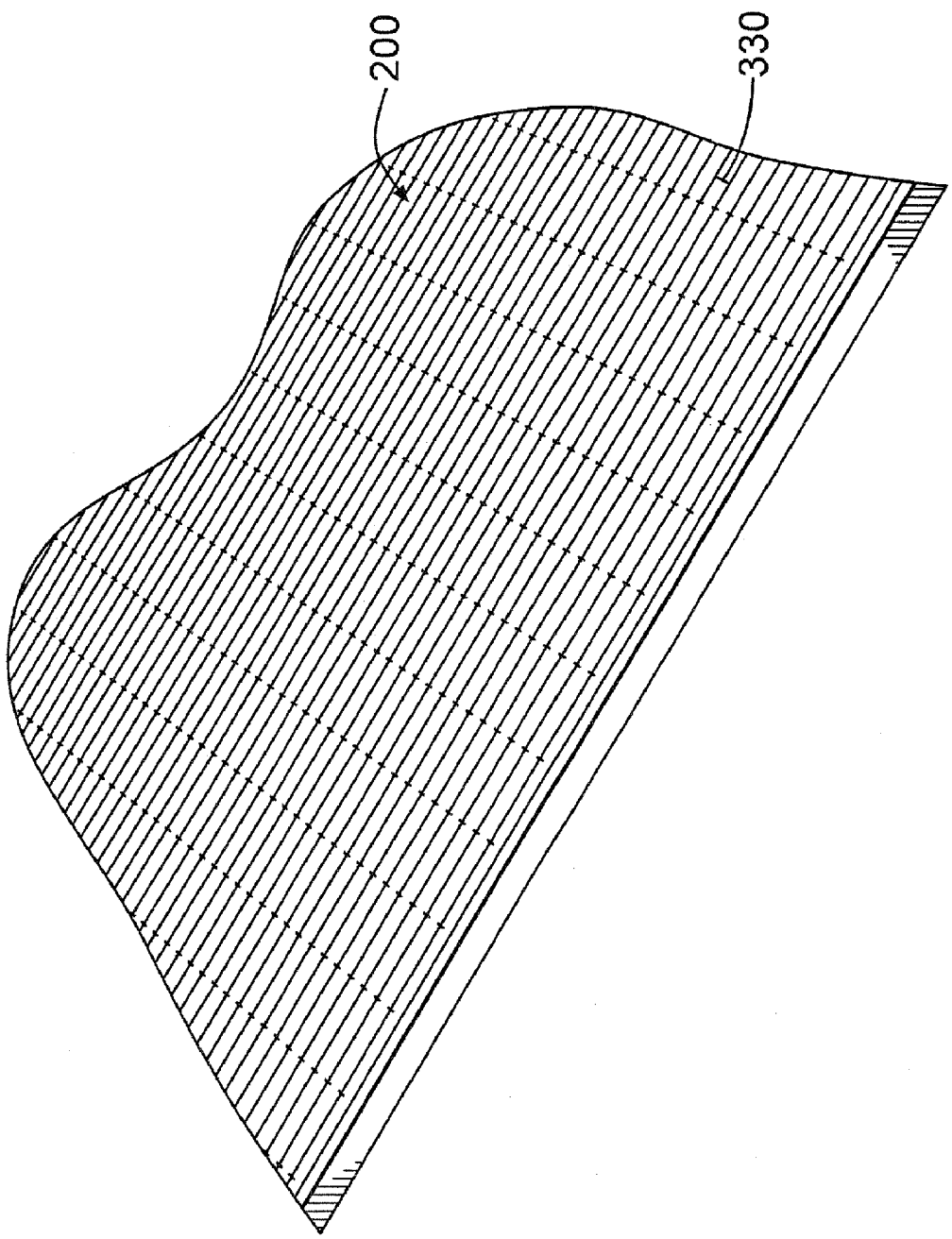

FIGS. 3A-3C illustrate various views of an embodiment of the flat coil 200 of FIG. 2, clearly showing the spacing between the coil turns, in accordance with various aspects of the present invention. The coil 200 shown in FIG. 3A is mounted on a surface 310 (e.g., a plywood board) using plastic clips to secure the wiring of the coil 200. FIG. 3B shows a curved section of the coil 200 with the spacing 320 between the curved segments being about one inch. FIG. 3C shows a straight section of the coil 200 with the spacing 330 between the straight and parallel segments being about one inch.

Figure 4:
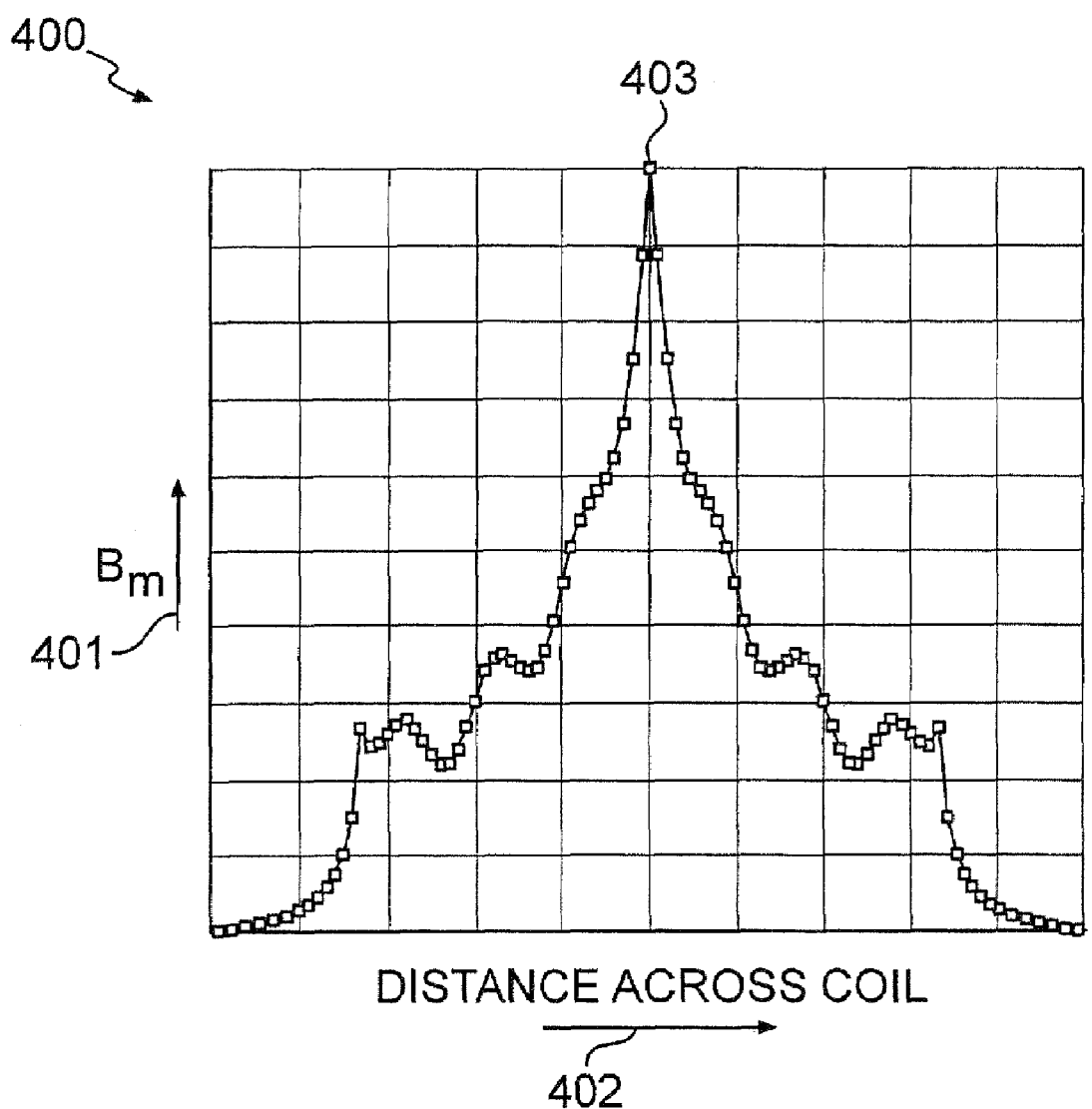
FIG. 4 illustrates an exemplary simulated graph of how a magnetic field intensity generated by the coil of FIG. 2 may be expected to vary non-linearly across a spatial dimension of the coil of FIG. 2, in accordance with various aspects of the present invention.

FIG. 4 illustrates an exemplary simulated graph 400 of how a magnetic field intensity $B_m$ 401 generated by the coil 200 of FIG. 2 may be expected to vary non-linearly across a spatial dimension 402 of the coil of FIG. 2 (distance across coil), in accordance with various aspects of the present invention. The peak magnetic intensity 403 occurs at the center of the coil 200. It is the configuration of the coil (e.g., shape, dimensions, spacing) that largely determines the shape of the spatially non-uniform magnetic field intensity. For example, the graph 400 of FIG. 4 may represent the variation in magnetic field intensity $B_m$ across the width dimension 240 of the coil 200 and through a first center axis 250 of the coil 200 (see FIG. 2).

Figure 5:
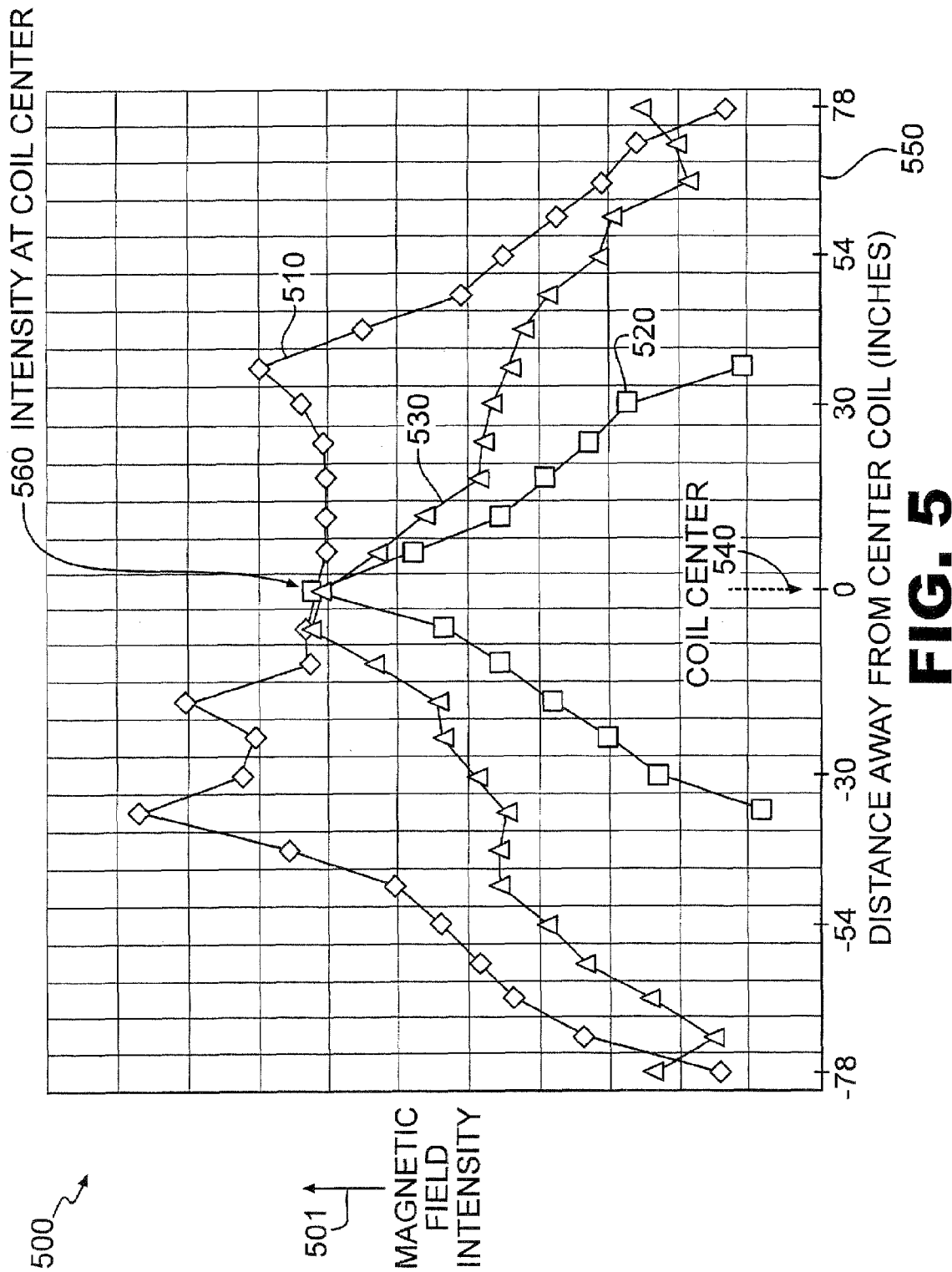
FIG. 5 illustrates an exemplary graph of measured data of how a magnetic field intensity generated by the coil of FIGS. 3A-3C varies across three spatial dimensions of the coil of FIGS. 3A-3C, in accordance with various aspects of the present invention.

FIG. 5 illustrates an exemplary graph 500 of measured data of how a magnetic field intensity 501 generated by the coil 200 of FIGS. 3A-3C varies across three spatial dimensions of the coil 200 of FIGS. 3A-3C, in accordance with various aspects of the present invention. The data set 510 shows the variation in measured magnetic field intensity above (e.g., 18 inches) the coil 200 and across the length dimension 260 of the coil 200 along the axis 265 which includes the physical center point 205 of the coil 200 (see FIG. 2). The coil center 540 is shown on the distance axis 550 in FIG. 5.

The data set 520 shows the variation in measured magnetic field intensity above (e.g., 18 inches) above the coil 200 and across the width dimension 240 of the coil 200 along the axis 250 which includes the physical center point 205 of the coil 200. The data set 530 shows the variation in measured magnetic field intensity above (e.g., 18 inches) the coil 200 and across a diagonal dimension of the coil 200 along the axis 270 which includes the physical center 205 of the coil 200.

The direction of the magnetic field intensities 510, 520, and 530 shown in the graph 500 is perpendicular to the flat surface of the coil 200. The absolute magnitude of the magnetic field intensities is a function of distance away from the surface or plane of the coil. In general, the magnetic field intensity decreases at points further away from the surface or plane of the coil. Notice that the magnetic field intensity 560 at the physical center of the coil is the same for all three data sets 510, 520, and 530 since the center corresponds to the same physical point in all three cases.

For example, if the coil 200 is placed flat and just beneath the bottom surface of a swimming pool (e.g., 1 to 30 inches), the magnetic field intensity 501 of the data sets 510, 520, and 530 will emanate above the coil into the water of the pool. As a swimmer swims through the pool across the coil (e.g., parallel to the surface of the coil), the swimmer will experience the magnetic variations of the magnetic field generated by the coil which stimulate the swimmer's immune system. In accordance with an embodiment of the present invention, the magnetic field is a pulsed magnetic field having a pulsed frequency of between 0.5 and 30 Hertz, and the intensity of the magnetic fields 510, 520, and 530 at a predetermined distance from the surface of the coil (e.g., 18 inches) vary through a range of about 0.5 to 30 Gauss across at least one spatial dimension of the coil 200. The electric current generator may comprise a programmable subsystem (e.g., a programmable logic controller or a computer-based subsystem such as a personal computer) which may control the frequency and intensity of the current pulses and, therefore, of the magnetic energy pulses.

Figure 6:
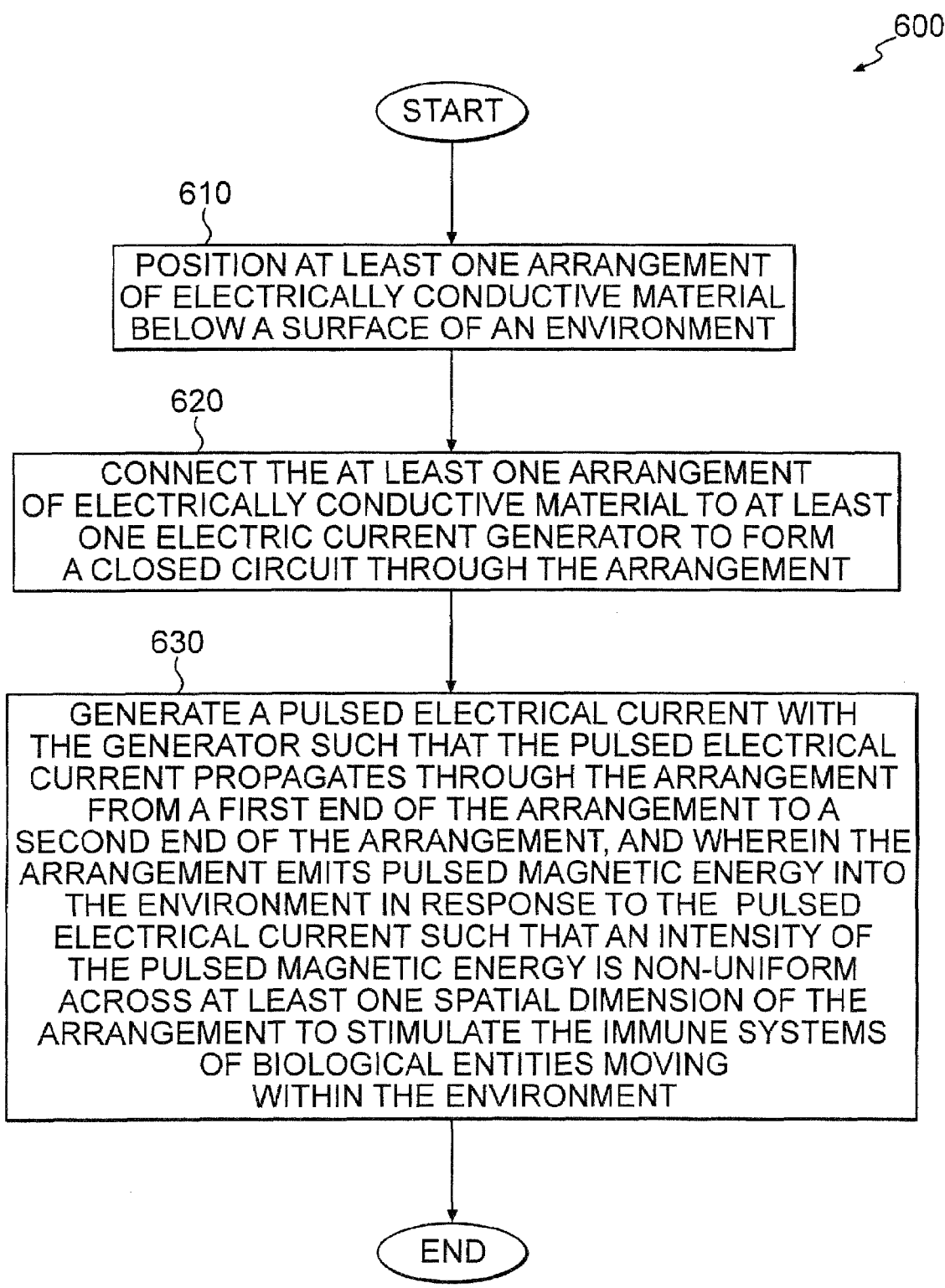
FIG. 6 is a flowchart of an embodiment of a method to stimulate immune systems of biological entities in an environment, in accordance with various aspects of the present invention.

FIG. 6 is a flowchart of an embodiment of a method 600 to stimulate immune systems of biological entities in an environment, in accordance with various aspects of the present invention. In step 610, at least one arrangement of electrically conductive material is positioned below a surface of an environment (for example, referring to FIG. 1, the coil 16 is positioned below the surface of the aquatic environment 12). In step 620, the at least one arrangement of electrically conductive material is connected to at least one electric current generator to form a closed circuit through the arrangement (for example, referring to FIG. 1, the ends 17 and 19 of the coil 16 are connected to electric terminals of the generator 14). In step 630, a pulsed electrical current is generated with the generator such that the pulsed electrical current propagates through the arrangement from a first end (e.g., end 19 in FIG. 1) of the arrangement to a second end (e.g., end 17 in FIG. 1) of the arrangement, and wherein the arrangement emits pulsed magnetic energy into the environment in response to the pulsed electrical current such that an intensity of the pulsed magnetic energy is non-uniform across at least one spatial dimension of the arrangement (e.g., see the non-uniform magnetic fields of FIGS. 4 and 5) to stimulate the immune systems as the biological entities move within the environment.

Figure 7:
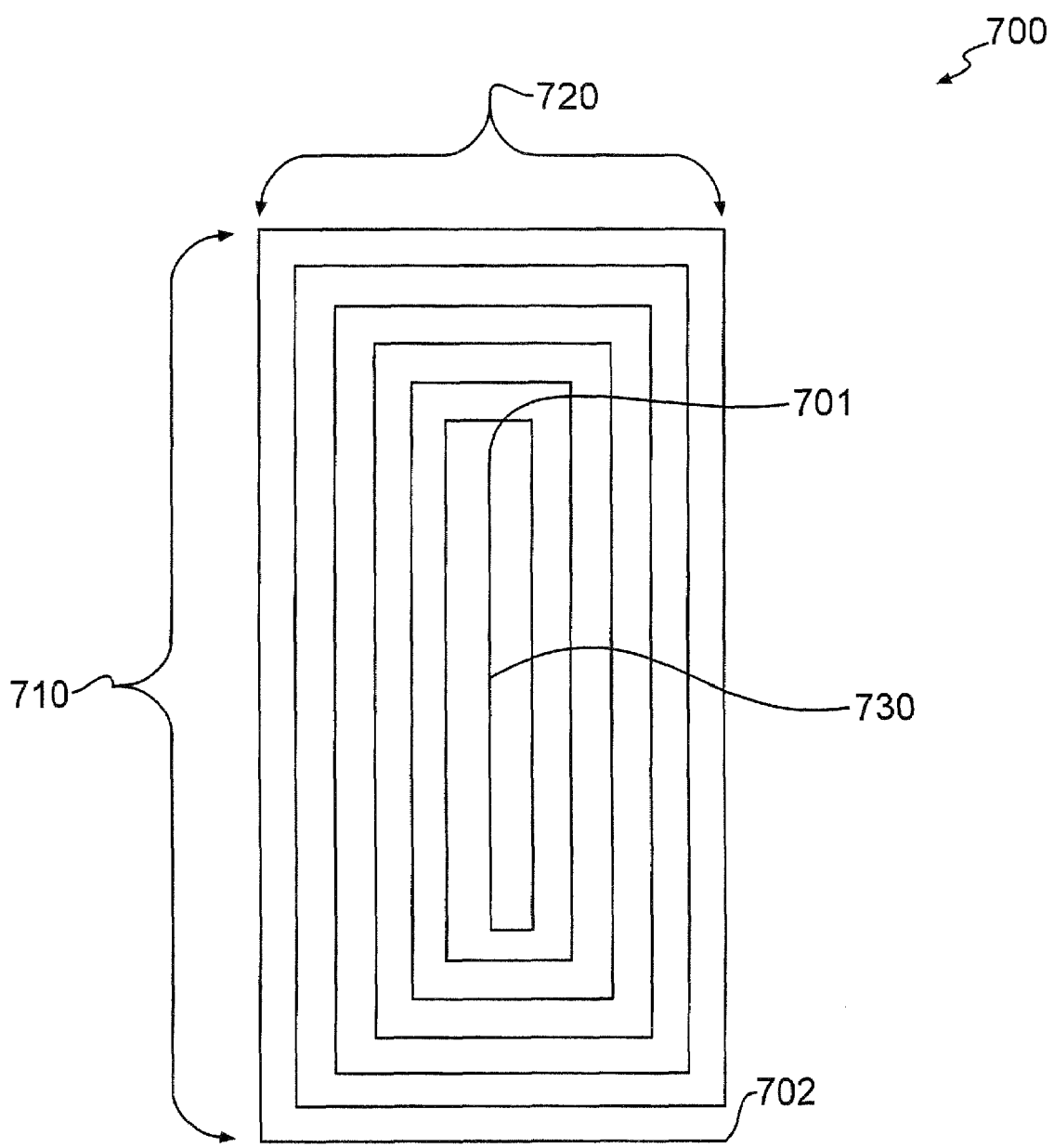
FIG. 7 illustrates a second exemplary embodiment of a flat coil used to generate magnetic energy, in accordance with various aspects of the present invention.

FIG. 7 illustrates a second exemplary embodiment of a flat coil 700 used to generate magnetic energy, in accordance with various aspects of the present invention. The coil 700 has a first end 701 and a second end 702 and comprises a first plurality of vertically oriented, parallel straight segments 710 of conductive wire and a second plurality 720 of horizontally oriented, parallel straight segments 720 of conductive wire which are substantially perpendicular to the first plurality of segments. The coil 700 is a continuous wire, winding outward from a central position 730 of the coil 700 in substantially a single spatial plane forming a flat, rectangular coil (i.e., a coil forming a flat, rectangular surface). The coil 700 of FIG. 7 is similar to the coil 200 of FIG. 2 except the curved segments of FIG. 2 are replaced with the straight segments 720 of FIG. 7 and the straight segments 710 are not all of the same length.

Figure 8:
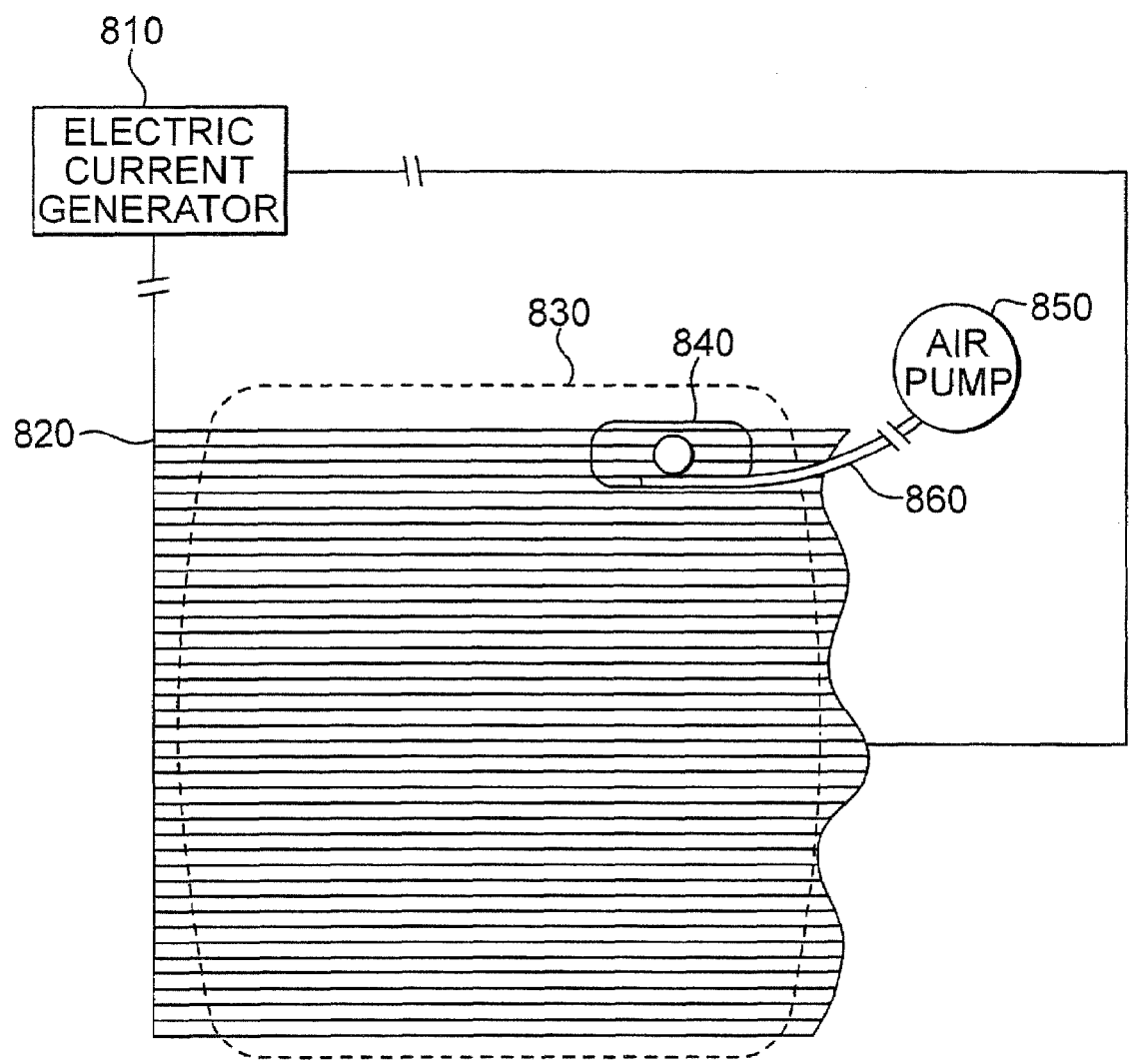
FIG. 8 illustrates a second exemplary embodiment of a system for applying pulsed magnetic energy to a stock pen environment, in accordance with various aspects of the present invention.

Referring now to FIG. 8, there is shown a second exemplary embodiment a system of the present invention, illustrating the application of pulsed magnetic energy to livestock animal pens. In this second embodiment, there is a stock pen 830 which can be used to retain any type of livestock animal or poultry. Further, it should be understood that such a stock pen can be enclosed in buildings or open fields. Electrical wiring 820 extends below the surface and laterally across first stock pen 830 to cover at least a substantial area of stock pen 830. The configuration of the electrical wiring 820 includes a plurality of substantially parallel segments of conductive material (e.g., segments of wiring) forming a flat, substantially rectangular grid. As in the first embodiment 10 of FIG. 1, electrical wiring 820 is comprised of electrical wiring having neutral insulating materials, and is placed under the surface of the selected area at a preferred depth of 1 to 30 inches. Electric current generator 810 generates and transmits pulsed electric currents through electric wiring 820. In accordance with an embodiment of the present invention, the width-to-length ratio of the substantially rectangular grid is between 0.4 and 0.8.

Optionally, this system may also include a water tank 840 for the watering of the animals. An air pump 850 may be used to pump air into the water tank 840 through hose 860. Aeration of water tank 840 by pump 850 increases the oxygen concentration of the water held within water tank 840.

In the embodiment of FIG. 8, the electrical wiring 820 forms a type of horizontal grid configuration across the stock pen 830. Pulsed current flows from the generator 810 through the various branches of the grid of wiring 820 and back to the generator 810, emitting pulsed magnetic energy (i.e., magnetic fields) into the environment of the stock pen 830. If the stockyard is enclosed, the electric wiring is buried at a depth between 1 and 30 inches within the dirt or other flooring material, such as concrete, for example. Again, a spatially non-uniform magnetic field is generated across the grid. However, the non-uniformity may be substantially different from that shown in FIGS. 4 and 5 due largely to the different configuration of the wiring 820 from that of the coil 200 of FIG. 2. However, a coil of the configuration of that of FIG. 1 or FIG. 2, or other configurations, could be used in the stockyard environment instead.

Figure 9:
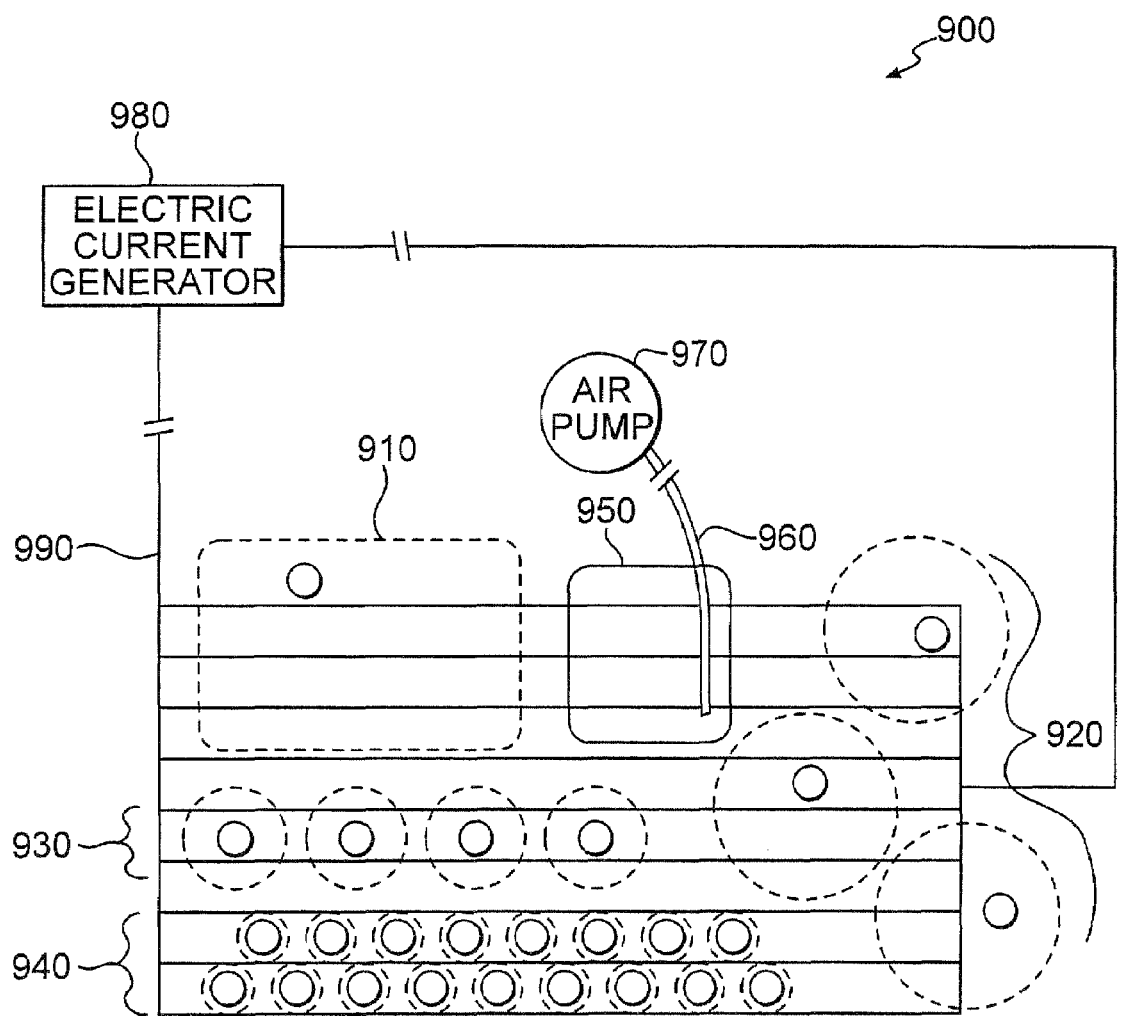
FIG. 9 illustrates a third exemplary embodiment of a system for applying pulsed magnetic energy to a garden environment, in accordance with various aspects of the present invention.

Now referring to FIG. 9, there is shown a third exemplary embodiment of a system of the present invention illustrating the application of pulsed magnetic energy to a plant bio-system 900, such as a garden. The plant based bio-system may include, for example, a grain plot 910, fruit or other trees 920, plants 930 and/or flowers 940. The plants may either be grown within the ground itself or within planting containers such as pots and the like. The environment 900 may optionally also include a water reservoir 950, which is aerated by hose 960 and air pump 970 to increase the oxygen concentration of the water held within reservoir 950. Pulsed magnetic energy is generated by an electric current generator 980 applying pulsed currents to electric wiring grid 990. Electric wiring grid 990 is positioned to cover at least a substantial portion of environment 900, and is placed below the surface of environment 900, at a depth of 1 to 30 inches. The plants affected by the application of the pulsed magnetic energy exhibit improved physiological effects such as improved and more rapid growth, and better overall health for example.

Figure 10:
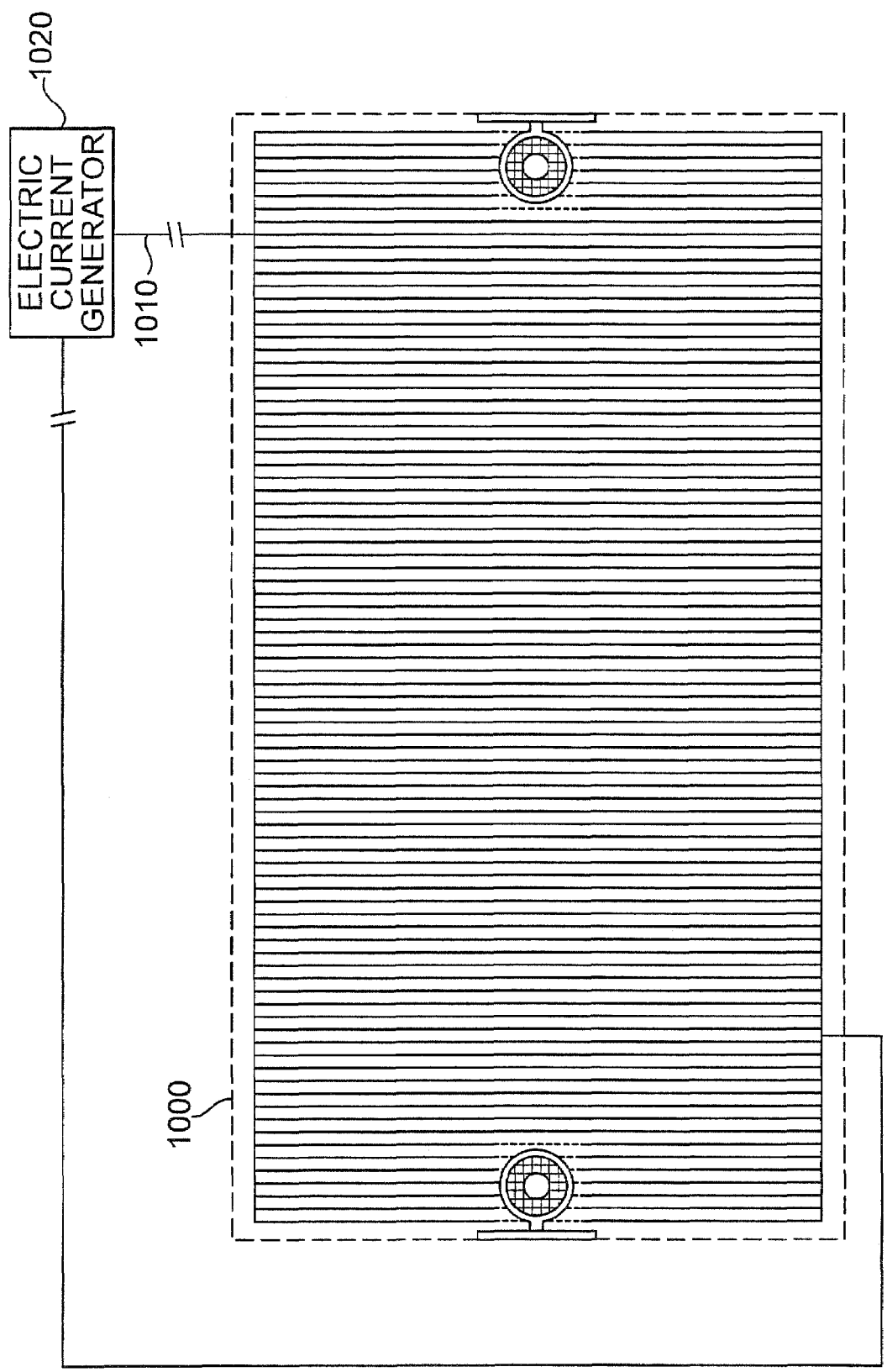
FIG. 10 illustrates a fourth exemplary embodiment of a system for applying pulsed magnetic energy to a sports environment, in accordance with various aspects of the present invention.

Shown in FIG. 10 is yet another exemplary embodiment of the present invention, illustrating applying magnetic energy to an athletic playing surface 1000, such as, for example a basketball court, a football field, a soccer field, a swimming pool, playgrounds or other playing surfaces. Electrical wiring 1010 is placed below playing surface 1000 at a preferred depth of between 1 and 30 inches. Electrical current generator 1020 generates and conducts electrical currents through electric wiring 1010 to create and diffuse the resultant magnetic energy throughout playing surface 1000. The magnetic energy is applied to those persons playing or competing on playing surface 1000. Upon application of the magnetic energy, humans may experience higher energy levels for longer periods of time, reduced fatigue, less muscle strain and soreness, in addition to increased concentration and precision in playing the particular sport.

Figure 11:
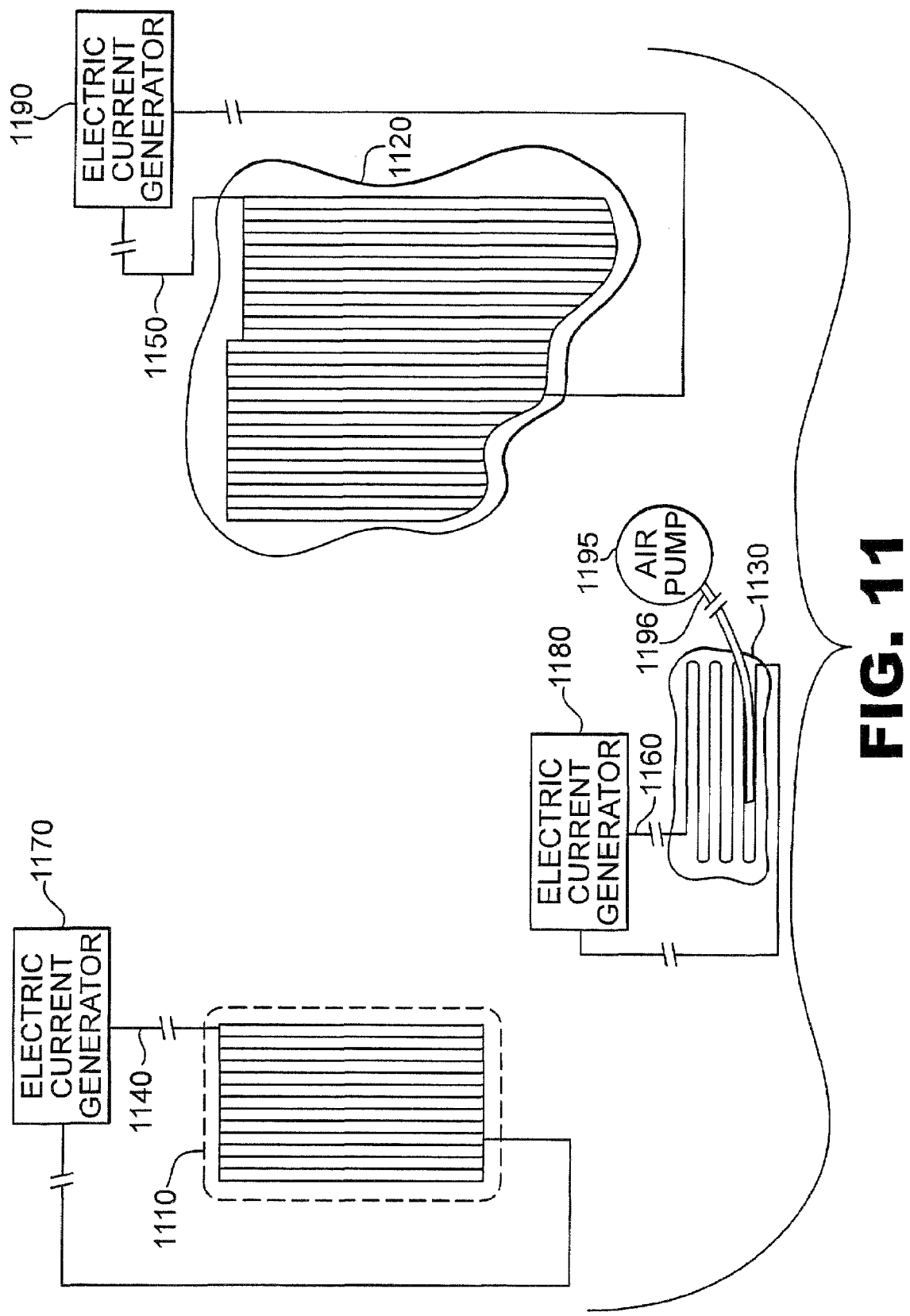
FIG. 11 illustrates a fifth exemplary embodiment of a system for applying pulsed magnetic energy to a golf course environment, in accordance with various aspects of the present invention.

Referring now to FIG. 11, there is shown yet another exemplary embodiment of the present invention, illustrating application of magnetic energy to a golf course hole. This embodiment includes a tee box 1110, a green 1120 and/or optionally a water reservoir 1130. Below tee box 1110 is placed electrical wiring 1140, which is placed at a depth of 1 to 30 inches. Electrical wiring 1150 is also placed below golf green 1120 at a preferred depth of 1 to 30 inches. If water reservoir 1130 is used, electrical wiring 1160 is positioned below the bottom of reservoir 1130 at a depth of 1 to 30 inches for emission of magnetic energy. Air pump 1195 and air hose 1196 may optionally be used to pump air into the water reservoir 1130 to increase the oxygen content. Treated water from reservoir 1130 may be used to water the golf course fairways, greens, or other plants associated with the course as to achieve the benefits as described above in relation to the plant based bio-system embodiment. Electric current generators 1170, 1180 and 1190 produce pulsed electric currents such that magnetic energy is emitted from electrical wiring 1140, 1160, and 1150 respectively. Optionally, a single generator can control the emission of magnetic energy from electrical wiring 1140, 1160, and 1150. As with the above described embodiments, electric current generators 1170, 1180 and 1190 cause magnetic energy to be emitted having magnetic field components about in the range of 0.5 to 30 Gauss, and the frequency range of the pulses is between 0.5 and 30 Hertz.

Effects seen through application of the pulsed magnetic energy to a grass surfaces such as soccer fields, play grounds, football fields, golf greens and tee boxes include more rapid and healthier growth of grass, faster regeneration or repair of divots and ball marks, fewer attacks to these grasses by pests as the grasses are healthier. The human players experience gentle invigoration, increased energy, greater concentration, and less muscle soreness or strain. Increased mental activity and faster healing of wounds has also been noted. Sporting equipment such as golf clubs are not affected by the application of magnetic energy because no sustained electrical current is conducted to the metal portions of the clubs.

In use with any of the above embodiments, the characteristics of the magnetic energy remain the same, that is the magnetic energy having magnetic field components about in the range of 0.5 to 30 Gauss, and the frequency range of the pulses between 0.5 and 30 Hertz. In application of pulsed magnetic energy to humans, the magnetic field strength may be adjusted to vary between 4 to 8 Gauss. The placement of the electrical wiring below the surface of the selected area is adjusted to accommodate these parameters. Further, it is important to note that the spacing and arrangement of the electric wiring in the above described embodiments may be altered to achieve certain desired effects.

Figure 12:
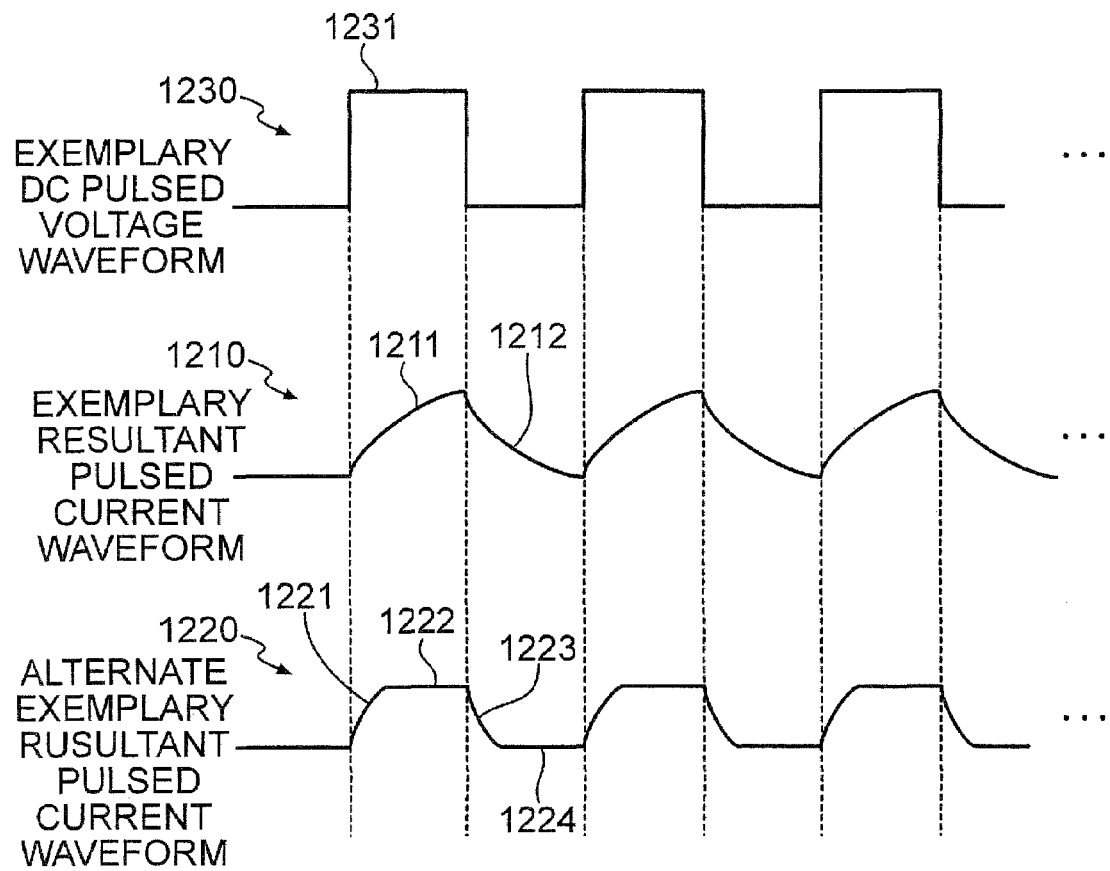
FIG. 12 illustrates exemplary resultant current pulses that may be produced in the coil of FIG. 2 when applying an exemplary DC pulsed voltage waveform to the coil of FIG. 2, in accordance with an embodiment of the present invention.

FIG. 12 illustrates exemplary resultant current pulses 1210 and 1220 that may be produced in the coil 200 of FIG. 2 when applying an exemplary DC pulsed voltage waveform 1230 to the coil 200 of FIG. 2, in accordance with an embodiment of the present invention. The pulsed voltage waveform 1230 shown in FIG. 12 is a square voltage waveform having a 50% duty cycle. Other duty cycles are possible as well, in accordance with various embodiments of the present invention. The pulsed voltage waveform 1230 is applied to the coil 200 by a generator (e.g., generator 14 of FIG. 1).

The frequency of the pulsed voltage waveform 1230 may be, for example, anywhere between 0.1 Hz and 30 Hz. Depending on the various parameters (e.g., the voltage level, the time constant, the pulsed frequency, etc.) of the system, the resultant pulsed current waveform in the coil may look like that of waveform 1210. Referring to the pulsed current waveform 1210, as the voltage level of the pulsed voltage waveform 1230 increases, the current level in the coil will begin to increase as seen in the segment 1211 of the pulsed current waveform 1210. The curved nature of the rising current level of the segment 1211 is due, at least in part, to the time constant of the system (including the coil) which is determined by inductive, capacitive, and resistive factors of the system. In the pulsed current waveform 1210, the current level rises continuously until the voltage level of the driving pulsed voltage waveform drops off.

When the voltage level of the pulsed voltage waveform 1230 decreases, the current level in the coil will begin to decrease as seen in the segment 1212 of the pulsed current waveform 1210. Again, the curved nature of the falling current level of the segment 1212 is due, at least in part, to the time constant of the system. In the pulsed current waveform 1210, the current level decreases continuously until the voltage level of the driving pulsed voltage waveform again rises. For example, the peak voltage level of the DC pulsed voltage waveform 1230 may be 80 VDC and the resultant peak current level of the pulsed current waveform 1210 may be 100 amps.

Referring to the pulsed current waveform 1220, as the voltage level of the pulsed voltage waveform 1230 increases, the current level in the coil will begin to increase as seen in the segment 1221 of the pulsed current waveform 1220. Again, the curved nature of the rising current level of the segment 1221 is due, at least in part, to the time constant of the system. In the pulsed current waveform 1220, the current level rises and then flattens off to a peak current level 1222 well before the voltage level of the pulsed voltage waveform drops off. This flattening off tends to occur when the peak voltage level 1231 is relatively low. The lower peak voltage level 1231 means that the current will not build to as high a level as it would with a higher peak voltage level driving the coil. Therefore, the pulsed current waveform 1220 reaches its peak level sooner and stays there.

When the voltage level of the pulsed voltage waveform 1230 decreases, the current level in the coil will begin to decrease as seen in the segment 1223 of the pulsed current waveform 1220. Again, the curved nature of the falling current level of the segment 1223 is due, at least in part, to the time constant of the system. In the pulsed current waveform 1220, the current level decreases to a zero current level 1224 well before the voltage level of the pulsed voltage waveform increases again. Again, this flattening off tends to occur when the peak voltage level 1231 is relatively low. That is, the current level does not have as far to fall since the peak current level was relatively low. Therefore, the current level reaches zero sooner and flattens off. For example, the peak voltage level of the DC pulsed voltage waveform 1230 may be 20 VDC and the resultant peak current level of the pulsed current waveform 1210 may be 10 amps.

Figure 13:
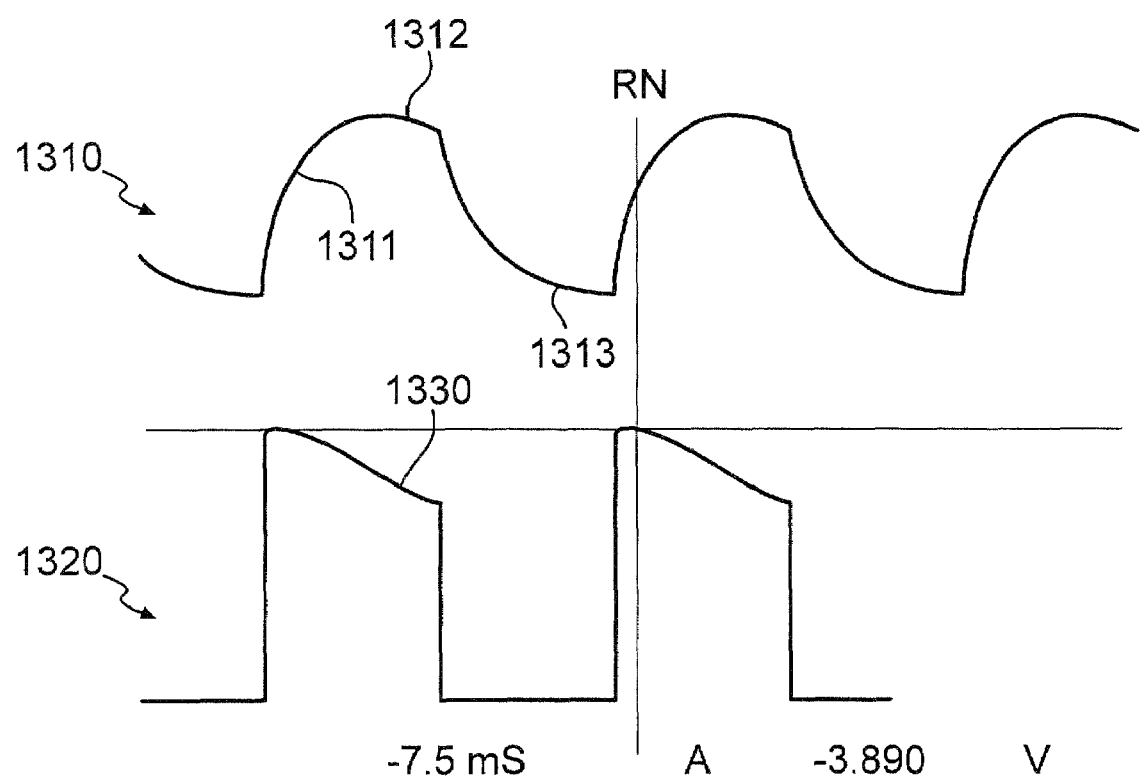
FIG. 13 illustrates exemplary resultant current pulses produced in the coil of FIGS. 3A-3C when applying an exemplary DC pulsed voltage waveform to the coil of FIGS. 3A-3C, in accordance with an embodiment of the present invention.

FIG. 13 illustrates exemplary resultant current pulses 1310 produced in the coil 200 of FIGS. 3A-3C when applying an exemplary DC pulsed voltage waveform 1320 to the coil 200 of FIGS. 3A-3C, in accordance with an embodiment of the present invention. The pulsed voltage waveform 1320 shown in FIG. 13 is a pseudo-square voltage waveform having a 50% duty cycle. Other duty cycles are possible as well, in accordance with various embodiments of the present invention. The pulsed voltage waveform 1320 tends to droop over the segment 1330 due to the load the coil provides to the generator. Therefore, the pulsed voltage waveform 1320 is not perfectly square.

The frequency of the pulsed voltage waveform 1320 may be, for example, anywhere between 0.1 Hz and 30 Hz. Depending on the various parameters (e.g., the voltage level, the time constant, the pulsed frequency, etc.) of the system, the resultant pulsed current waveform in the coil may look like that of waveform 1310. Referring to the pulsed current waveform 1310, as the voltage level of the pulsed voltage waveform 1320 increases, the current level in the coil will begin to increase as seen in the segment 1311 of the pulsed current waveform 1310. The curved nature of the rising current level of the segment 1311 is due, at least in part, to the time constant of the system (including the coil) which is determined by inductive, capacitive, and resistive factors of the system. In the pulsed current waveform 1310, the current level rises continuously until the voltage level of the driving pulsed voltage waveform begins to droop. There is a time delay, however, between when the voltage level begins to droop and when the current level begins to decrease slightly over the segment 1312.

When the voltage level of the pulsed voltage waveform 1320 drops off, the current level in the coil will begin to decrease as seen in the segment 1313 of the pulsed current waveform 1310. Again, the curved nature of the falling current level of the segment 1313 is due, at least in part, to the time constant of the system. In the pulsed current waveform 1310, the current level decreases continuously until the voltage level of the driving pulsed voltage waveform again rises.

In accordance with various embodiments of the present invention, the systems described herein may be used by incrementing and/or decrementing the pulsed frequency over time. For example, in accordance with an embodiment of the present invention, the pulsed frequency may start at 0.5 Hz and be incremented every one minute by 0.5 Hz until reaching 28 Hz. Then the pulsed frequency may be decremented from 28 Hz back down to 0.5 Hz at a frequency step of 0.5 Hz every minute. Other methods of varying the pulsed frequency over time are possible as well and may be tailored to certain physiological conditions to be treated by stimulating the immune system.

In summary, a method and systems are disclosed for stimulating the immune systems of biological entities in an environment. A magnetic energy field is generated such that the magnetic energy field varies non-uniformly in intensity across at least one spatial dimension of the environment. The magnetic energy field is generated using an electric current generator which is connected to a coil or other alternate arrangement of conductive material such as wire. The coil or arrangement is typically placed beneath a surface of the environment. The magnetic energy field is pulsed at a predetermined frequency.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A system for stimulating immune systems of biological entities, said system comprising:
   at least one electric current generator providing a source of pulsed electrical current;
   at least one continuous coil of electrically conductive material having a first end and a second end, both of said ends being connected to said at least one generator to form a closed circuit such that said at least one coil emits a spatially non-uniform pulsed magnetic field in response to said pulsed electrical current, and wherein a configuration of said at least one coil comprises a plurality of turns of said conductive material in substantially a single spatial plane, and wherein said coil has an overall width-to-length ratio of between 0.4 and 0.8; and
   an environment containing said at least one continuous coil, wherein said environment includes at least one of a livestock yard, a garden, an orchard, an athletic ground, and a play ground.

2. The system of claim 1 wherein an intensity of said magnetic field varies non-linearly across at least one spatial dimension of said at least one coil, said at least one spatial dimension being parallel to said single spatial plane.

3. The system of claim 2 wherein said intensity of said magnetic field varies through a range of about 0.5 to 30 Gauss across said at least one spatial dimension at a predetermined distance from said spatial plane.

4. The system of claim 1 wherein a pulse frequency of said pulsed magnetic field is in a range of 0.5 to 30 Hertz.

5. The system of claim 4 wherein said pulse frequency is incremented over time.

6. The system of claim 4 wherein a duty cycle of said pulse frequency is approximately 50%.

7. The system of claim 4 wherein said pulse frequency is decremented over time.

8. The system of claim 1 wherein said at least one coil is positioned at a depth of between 1.0 and 30 inches below a surface of said environment.

9. The system of claim 1 wherein said at least one coil is insulated by a non-conductive material.

10. The system of claim 1 wherein said at least one electric current generator comprises a programmable subsystem which may be programmed to control at least an intensity and a pulsed frequency of said electrical current.

11. The system of claim 1 wherein said width-to-length ratio is approximately 0.6.

12. The system of claim 1 wherein a maximum intensity of said spatially non-uniform pulsed magnetic field occurs approximately at a center of said coil.

* * * * *